United States Patent
Miyake et al.

(10) Patent No.: US 8,038,596 B2
(45) Date of Patent: Oct. 18, 2011

(54) OBSERVATION APPARATUS THAT DETECTS POSITION OF A TREATMENT TOOL FROM AN IMAGE

(75) Inventors: Yoichi Miyake, Sakura (JP); Tatsuo Igarashi, Chiba (JP); Harufumi Makino, Chiba (JP); Toshiya Nakaguchi, Funabashi (JP); Hiroshi Fujita, Saitama (JP)

(73) Assignee: Fujifilm Corporation, Tokyo (JP)

( * ) Notice: Subject to any disclaimer, the term of this patent is extended or adjusted under 35 U.S.C. 154(b) by 1355 days.

(21) Appl. No.: 11/602,362

(22) Filed: Nov. 21, 2006

(65) Prior Publication Data

US 2007/0197865 A1    Aug. 23, 2007

(30) Foreign Application Priority Data

Feb. 21, 2006    (JP) ................. 2006-044377

(51) Int. Cl.
*A61B 1/04* (2006.01)
(52) U.S. Cl. .......... 600/103; 600/109; 600/168
(58) Field of Classification Search .......... 600/109, 600/112, 117, 118, 160, 167, 168, 173, 103; 348/65
See application file for complete search history.

(56) References Cited

U.S. PATENT DOCUMENTS

| 5,836,869 | A | 11/1998 | Kudo et al. | |
| 6,036,637 | A | 3/2000 | Kudo | |
| 7,684,851 | B2 * | 3/2010 | Miyake et al. | 600/424 |
| 2006/0050145 | A1 * | 3/2006 | Tanimoto | 348/68 |
| 2006/0074307 | A1 * | 4/2006 | Igarashi et al. | 600/434 |

FOREIGN PATENT DOCUMENTS

| JP | 8-164148 A | 5/1996 |
| JP | 10-276974 A | 10/1998 |
| JP | 8-336497 A | 12/1998 |
| JP | 2005-13557 A | 1/2005 |

OTHER PUBLICATIONS

Nakaguchi et al., Biomedical Engineering Symposium 2005, "Implementation of an Automatic Enlargement and Tracking System in Laparoscopic Surgery", pp. 1-13, (Sep. 2005).

* cited by examiner

*Primary Examiner* — John P Leubecker
(74) *Attorney, Agent, or Firm* — Birch, Stewart, Kolasch & Birch, LLP

(57) ABSTRACT

A body cavity observation apparatus includes a treatment tool to be inserted into a body cavity of a subject with an insertion tool as a guide, an observation section attached to an opening of a body wall of the subject, a monitor for displaying the body cavity captured by the observation section, and a marker position-detecting device for detecting a position of a marker part applied to the treatment tool or insertion tool from an image showing the body cavity captured by the observation section. The marker position-detecting device includes a pixel extracting device for extracting a group of pixels in the same color as the color of the marker part from the image and a calculation device for calculating a position of the barycenter of the group of pixels as a position of the marker part. The pixel extracting device extracts a pixel whose output value of a color component included in a color of the marker part among R, G, and B output values outputted from an image pickup device of the observation section is bigger than an output value of a color component that is not included in a color of the marker part by a predetermined threshold of the group of pixels.

3 Claims, 5 Drawing Sheets

OBSERVATION APPARATUS THAT DETECTS POSITION OF A TREATMENT TOOL FROM AN IMAGE

BACKGROUND OF THE INVENTION

1. Field of the Invention

The present invention relates to a body cavity observation apparatus, and more specifically to a body cavity observation apparatus that performs various treatments by displaying a subject's body cavity on a monitor.

2. Description of the Related Art

An abdominoscope apparatus, which is a body cavity observation apparatus, is an apparatus for piercing a surface of the patient's abdomen with a trocar (insertion tool) into the body cavity, inserting an inserting part of the abdominoscope with the trocar as a guide into the body cavity, and performing various treatments including adhesion treatment by displaying the presence of the adhesion in the body cavity, an observation object such as ovarian tumor, hysteromyoma and the like on a monitor. The abdominoscope is held on a moving holder attached to a fixed part at clinic and kept in a fixed state (for example, Japanese Patent Application Laid-Open No. 8-164148).

In the clinic treatment using the abdominoscope device, a position of the tip of a treatment tool placed inside the body cavity is detected, and the tip of the treatment tool is tracked so that the tip always appears at the center of an image on the monitor to observe the observation object, which is actually subject to treatment, in the center of the monitor image. A position-detecting device described in Japanese Patent Application Laid-Open No. 8-164148 includes a magnetic three-dimensional position sensor attached to a part of the abdominoscope outside the body cavity. The magnetic three-dimensional position sensor includes a magnetic source attached to the abdominoscope and a magnetic sensor attached to a treatment tool, and calculates a position of the treatment tip of the treatment tool placed inside the body from the location outside the body where the magnetic sensor is set in a coordinate transformation method by rotating/translating and obtains position information on the tip of the treatment tool placed inside the body cavity.

Japanese Patent Application Laid-Open No. 10-276974 applies a color marker part to the tip of a treatment tool, extracts the color marker part by converting brightness of a captured image into an independently calculated color space, and determines the extracted position as the tip position of the treatment tool tip.

SUMMARY OF THE INVENTION

The abdominoscope according to Japanese Patent Application Laid-Open No. 8-164148 has problems in that using of the magnetic three-dimensional position sensor as a position-detecting device makes the abdominoscope scaled large, and that additional provision of a machine called the magnetic three-dimensional sensor for the abdominoscope increases the cost of the entire abdominoscope device.

The present invention is adapted in view of the circumstances and intends to provide a body cavity observation apparatus, which can detect the tip of the treatment tool or the insertion tool with a simple configuration without providing a machine separately.

In order to achieve the abovementioned object, the invention described in the first aspect is a body cavity observation apparatus including a treatment tool to be inserted into a body cavity of a subject with an insertion tool as a guide, an observation section attached to an opening of a body wall of the subject, a monitor for displaying the body cavity captured by the observation section, and a marker position-detecting device for detecting a position of a marker part applied to the treatment tool or insertion tool from an image showing the body cavity captured by the observation section, wherein the marker position-detecting device includes a pixel extracting device for extracting a group of pixels in the same color as color of the marker part from the image, and a calculation device for calculating a position of the barycenter of the group of pixels as a position of the marker part.

According to the invention of the first aspect, a group of pixels in the same color as that of the marker part applied to the treatment tool or the insertion tool is extracted from an image showing a body cavity captured by the observation section by a pixel extracting device, and a position of the barycenter of the group of pixels is calculated by a calculating device as a position of the marker part. That enables the position of the marker part to be detected only by including circuits of the pixel extracting device and the calculating device into an image processing circuit so that the tip of the treatment tool can be detected with a simple configuration without additionally providing another machine.

The invention of the second aspect is the invention of the first aspect, wherein the pixel extracting device extracts a pixel whose output value of a color component included in a color of the marker part among R, G, and B output values outputted from an image pickup device of the observation section is bigger than an output value of a color component that is not included in a color of the marker part by a predetermined threshold or more as the group of pixels.

According to the invention of the second aspect, as the pixel extracting device extracts a pixel whose output value of a color component included in a color of the marker part among R, G, and B output values outputted from an image capturing device of the observation section is bigger than an output value of a color component that is not included in a color of a marker part by a predetermined threshold or more is extracted as the group of pixels, the pixel extracting device can extract a pixel that is actually desired to be extracted, i.e., a color of a marker part.

The invention of the third aspect is the invention of the first or the second aspect further including a trimming device for trimming an image to a predetermined region so that the position of the marker part calculated by the calculating device is placed at the center of the image, and a zooming device for zooming the trimmed predetermined region on the monitor by a predetermined magnification.

According to the invention of the third aspect, the trimming device trims the image to the predetermined region so that the marker part is placed at the center of the image, and then the zooming device zooms the image region by a predetermined magnification on the monitor. With such image processing, an image of a site that is actually desired to be observed can be easily zoomed and the marker part can be tracked without requiring a person to act on it.

The invention of the fourth aspect is the invention of the first or the second aspect, wherein the marker part is applied at least to two parts on the treatment tool or insertion tool, the body cavity observation apparatus includes: a trimming device for trimming an image to a predetermined region so that a position on a predetermined extension between two positions on the marker part calculated by the calculation device is placed at the center of the image, and a zooming device for zooming the trimmed predetermined region on the monitor by a predetermined magnification.

According to the invention of the fourth aspect, a trimming device trims an image to a predetermined region so that a position calculated by the calculation device, i.e., a position on a predetermined extension between two positions on the marker part is placed at the center of the image, and the zooming device zooms the trimmed predetermined region on the monitor by a predetermined magnification. With such image processing, the predetermined region can be predicted as an actual work area by a treatment tool, the predicted actual work area can be zoomed, and the predicted actual work area can be tracked.

With the body cavity observation apparatus according to the present invention, the pixel extracting device extracts a group of pixels in the same color as that of a marker part applied to the treatment tool or the insertion tool from an image showing a body cavity captured by the observation section and the calculating device calculates the position of the barycenter of the group of pixels as a position of the marker part so that the position of the marker part can be detected only by including circuits of the pixel extracting device and the calculating device into the image processing circuit. Therefore, the tip of the treatment tool or the insertion tool can be detected with a simple configuration without requiring a machine to be additionally provided.

DETAILED DESCRIPTION OF THE PREFERRED EMBODIMENTS

A preferred embodiment of the body cavity observation apparatus according to the present invention will be described with reference to the attached drawings.

Figure 1:
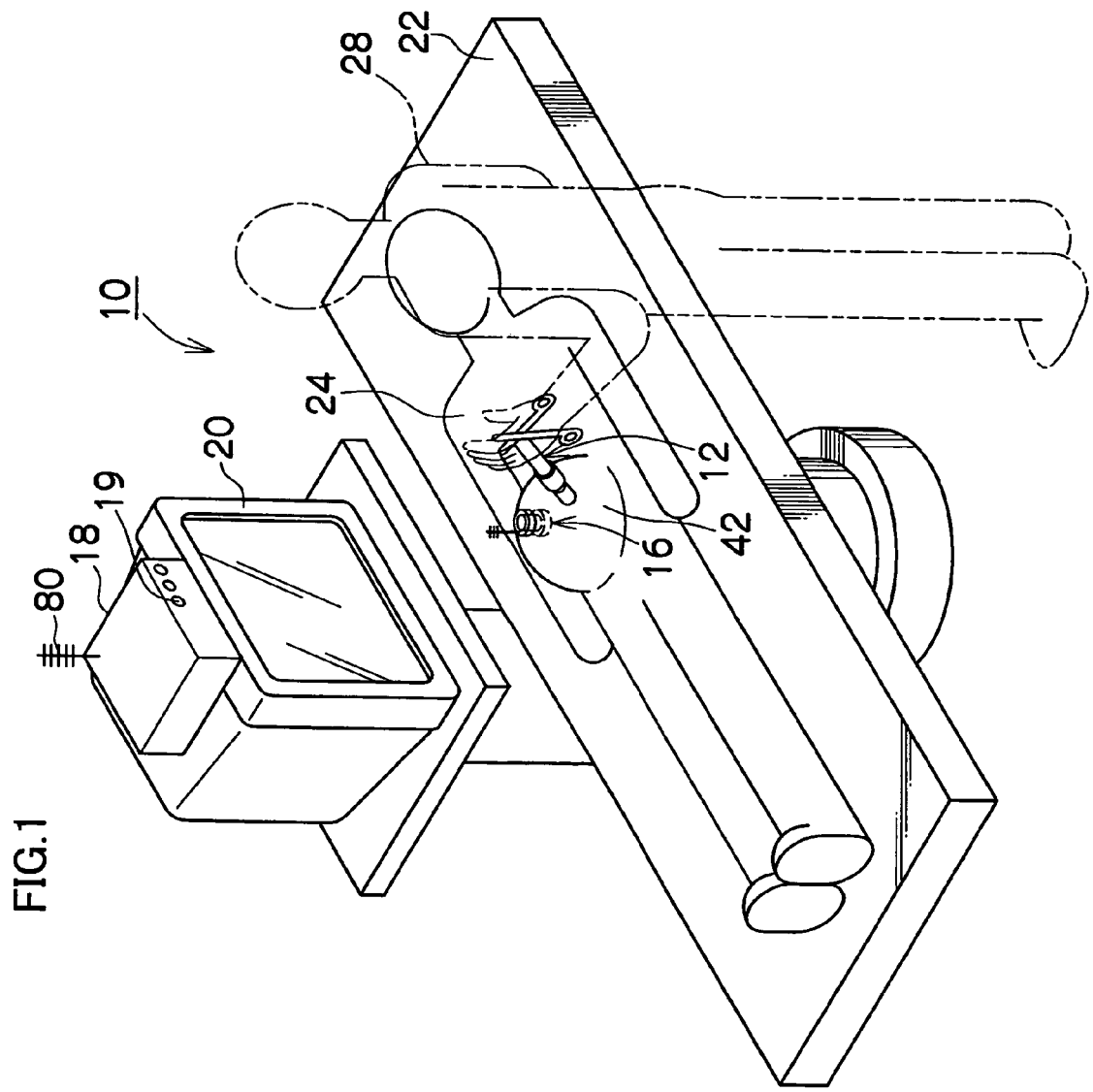
FIG. 1 is a system configuration diagram of a body cavity observation apparatus with an observation unit integrating an observation optical system.
Figure 2:
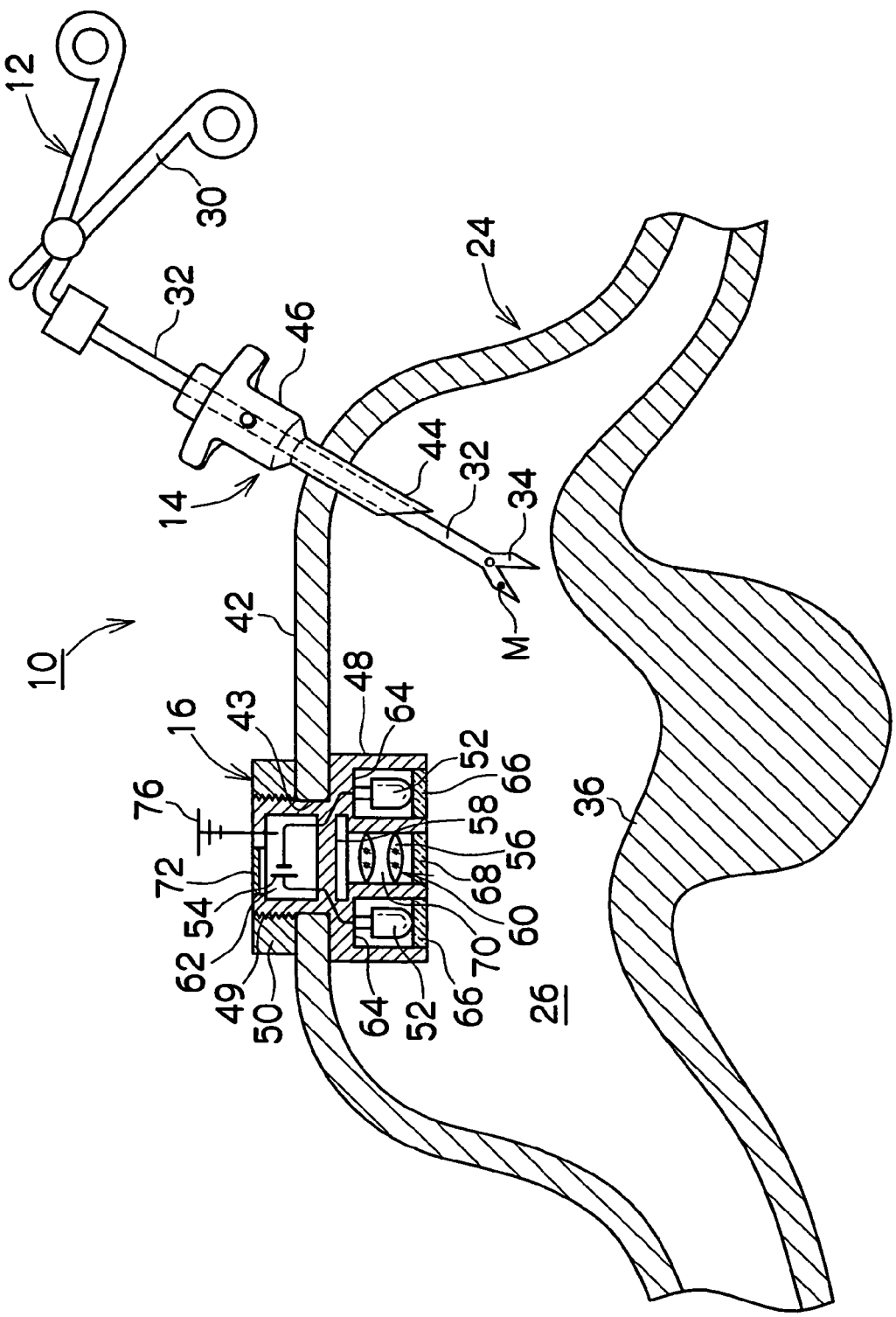
FIG. 2 is a schematic diagram showing a clinical state with the body cavity observation apparatus shown in FIG. 1.

FIG. 1 shows a system configuration diagram of the body cavity observation apparatus 10 according to an embodiment of the present invention. FIG. 2 shows a clinical state with the body cavity observation apparatus 10.

As shown in FIG. 1 and FIG. 2, the body cavity observation apparatus 10 includes a treatment tool 12, a trocar (insertion tool) 14, an observation unit (observation section) 16, an image signal processing device 18, a monitor 20 and the like. The observation unit 16 may be substituted by an endoscope or a hard mirror for capturing an image of the body cavity.

The treatment tool 12 is for treating an affected area inside the body cavity 26 of a subject 24 laid on an operating table 22. The treatment tool 12 has an operation section 30 for an operator 28 to operate. The treatment tool 12 is connected to the insertion section 32 at the tip of the operation section 30, with a clamp 34 is provided for the tip of the inserting section 32.

The inserting section 32 of the treatment tool 12 is inserted in the body cavity 26 with a trocar 14 pierced through a surface of the abdomen 42 of the subject 24 as a guide as shown in FIG. 2. The trocar 14 includes a metal hollow tube 44 with an acuminate tip and a soft supporting tube 46 provided for the base of the hollow tube 44. For the trocar 14 with such a configuration, a hollow tube 44 is inserted in the body cavity 26 as the operator 28 supports the supporting tube 46 and pierces the abdomen 42 with the acuminate tip of the hollow tube 44.

The observation unit 16 is made almost in a column form as shown in FIG. 1 and fixed to an opening 43, which is cut and opened on the abdomen 42, near the position where the trocar 14 pierces. The observation unit 16 includes a unit body 48 made in almost in a column form as shown in FIG. 2, and a nut section 50 that is screwed together with an external thread 49 of the unit body 48 and clamps an abdominal wall (abdominal skin) against the unit body 48. By clamping, the observation unit 16 is fixed to the opening part 43.

The unit body 48 has a plurality of light-emitting diodes 52, a battery 54, an observation optical system 60 with a lens 56 and a CCD (image pickup device) 58, and an image signal sending section 62 for wirelessly sending an image signal. A plurality of LEDs 52, 52 . . . are arranged on the circumference of the unit body 48 with its center axis as a center by even interval. A storage concave part 64 that stores the LEDs 52 is sealed by a plate 66 such as a transparent plate or a diffuse light plate. The observation optical system 60 is placed so that the optical axis matches the center axis of the unit body 48. The transparent plate 68 is arranged in front of the lens 56 of the observation optical system 60, with the transparent plate 68 sealing the storage concave part 70 of the observation optical system 60.

Figure 3:
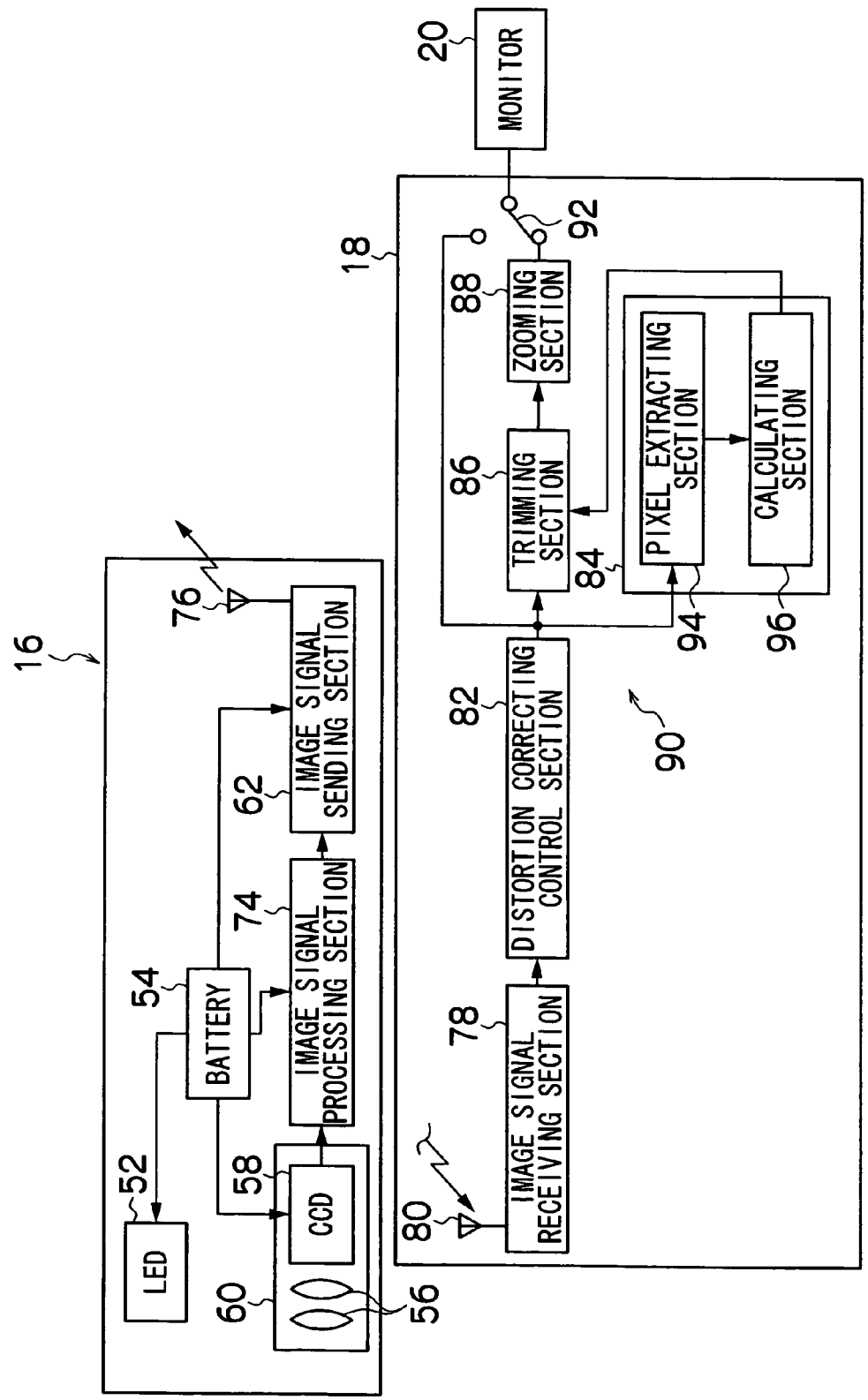
FIG. 3 is a block diagram showing a configuration of the body cavity observation apparatus shown in FIG. 1.

For the battery 54, a button battery is used in favor of its compactness. The battery 54 is exchanged with a new battery 54 as a cap 72 detachably attached to the surface of the unit body 48 is removed. As shown in FIG. 3, the battery 54 supplies power to the LEDs 52, the CCD 58, and the image signal sending unit 62, and also supplies power to an image signal processing section 74 which processes an output signal from the CCD 58 to an image signal. The image signal processing section 74 is also included in the unit body 48 shown in FIG. 2.

An observation unit 16 with such a configuration illuminates the observation object 36 with the LEDs 52, 52 . . . , and the light figure of the observation object is provided on the CCD 58 via the lens 56. Then, an output signal from the CCD 58 is processed into an image signal by the image signal processing section 74 and sent to the image signal processing device 18 shown in FIG. 1 from an antenna 76 of the image signal sending section 62. The observation unit 16 has a function of illuminating, capturing an image, and sending an image signal by the built-in battery 54.

The image signal sent to the image signal processing device 18 is received by the antenna 80 of the image signal processing receiving section 78 as shown in FIG. 3. Distortion characteristics of the lens 56 on the received image signal is corrected by the distortion correcting control section 82 and outputted to the marker tracking control section 90 including a marker position-detecting section (marker position-detecting device) 84, a trimming section (trimming device) 86, and a zooming section (zooming device) 88.

The marker tracking control section 90 will be described below.

As the observation unit 16 is fixed to the body wall opening part 43, the observation optical system 60 of the observation unit 16 shown in FIG. 2 with a view wide enough to look over the body cavity 26. If all the regions of the captured region that is captured by the observation optical system 60 with a wide view (for example, a viewing angle of 170 degrees) is displayed on the monitor 20, there is a problem in that an image of a site that is actually desired to be observed near the tip of the treatment tool or the trocar 14 shrinks.

In order to solve the problem, a marker (marker part) M in a color (for example, green) totally different from that of the body is applied to the clamp (tip) 34 of the treatment tool 12 as shown in FIG. 2. The position of the marker M is detected by the marker position-detecting section 84 of FIG. 3 in image processing by the marker tracking control section 90. The image is trimmed to a predetermined region by the trimming section 86 so that the marker M is placed at the center of the image. The image region is zoomed on the monitor 20 by the zooming unit 88 by a predetermined magnification. The zooming magnification is adjusted as a magnification adjustment knob 19 of the image signal processing machine 18 is operated. An image of a site that is actually desired to be observed can be displayed enlarged on the monitor 20 by such image processing, and thus, the abovementioned problem that occurs when an observation optical system with a wide view is used can be solved. The observation unit 16 can be used as it is fixed to the opening part of the body wall 43 without requiring an operator to operate on it, and thus, the number of operators can be reduced without causing any inconvenience to the clinical treatment. If the position of the marker M changes as the treatment tool 12 is operated, the marker M is always tracked by the marker position-detecting section 84, an image near the marker M can be always zoomed and observed. The marker M can be applied to the tip of the trocar 14.

The image signal processing device 18 of the embodiment has a selector switch 92. The selector switch 92 is for selectively switching an image signal to be outputted to the monitor 20 between an image signal with only distortion characteristics being corrected and an image signal that is of an automatically tracked and zoomed marker M. When the image signal is switched to the latter, the image near the marker M can be zoomed and observed on the monitor 20. When the image signal is switched to first, all the regions of the image captured by the observation optical system 60 with a wide view can be observed on the monitor 20. That is convenient in locating the position of the clamp 34 of the treatment tool 12 in the whole of the body cavity 26.

The marker detecting section 84 of the body cavity observation apparatus 10 of the embodiment includes a pixel extracting section (pixel extracting device) 94 and a calculating section (calculating device) 96.

The pixel extracting section 94 extracts a group of pixels in the same color as that of a green marker M added to the treatment tool 12 from an image showing the body cavity captured by the observation unit 16. The calculation unit 96 calculates the position of the barycenter of the group of pixels as a position of the marker M. That enables a position of the marker M to be detected only by including circuits of the pixel extracting section 94 and the calculating section 96 into the marker position-detecting section 84 so that the tip of the treatment tool 12 can be detected with a simple configuration without additionally providing a machine.

Specifically, the pixel extracting section 94 extracts a pixel whose output value of a color component included in a green color of the marker M among R, G, and B outputted values outputted from the CCD 58 of the observation unit 16 via an image signal sending section 62 is bigger than an output value of a color component that is not included in the green color of the marker M by a predetermined threshold or more as the group of pixels.

Next, an example of calculation by the calculation unit 96 will be described below.

The barycenter of a green color region $C_g$ is obtained by the expressions below, where a pixel value of the color c={r, g, b} on the coordinate (x, y) is f {x, y, c}.

$$C_g = \begin{bmatrix} C_{g,x} \\ C_{g,y} \end{bmatrix} \qquad \text{[Formula 1]}$$

$$= \begin{bmatrix} \dfrac{\sum_{i=1}^{W/5}\sum_{j=1}^{H/5} 5i \cdot h_g(5i, 5j)}{\sum_{i=1}^{W/5}\sum_{j=1}^{H/5} h_g(5i, 5j)} & \dfrac{\sum_{i=1}^{W/5}\sum_{j=1}^{H/5} 5j \cdot h_g(5i, 5j)}{\sum_{i=1}^{W/5}\sum_{j=1}^{H/5} h_g(5i, 5j)} \end{bmatrix}^t,$$

$$h_g(x, y) = \begin{cases} 1 & \text{if } f(x, y, g) > f(x, y, r) + t_{g,r} \text{ and} \\ & \quad f(x, y, g) > f(x, y, b) + t_{g,b} \\ 0 & \text{else} \end{cases}.$$

Here, $^t$ represents transposition, W and H represent the number of pixels in a horizontal direction and a vertical direction of the abdominoscope input image, respectively. "tg.r, tg.b" are threshold parameters to be used to detect green. The system performs detection for five pixels in both the vertical direction and the horizontal direction in calculating the barycenter to reduce the calculation cost. The detection may be performed for each pixel.

Figure 4:
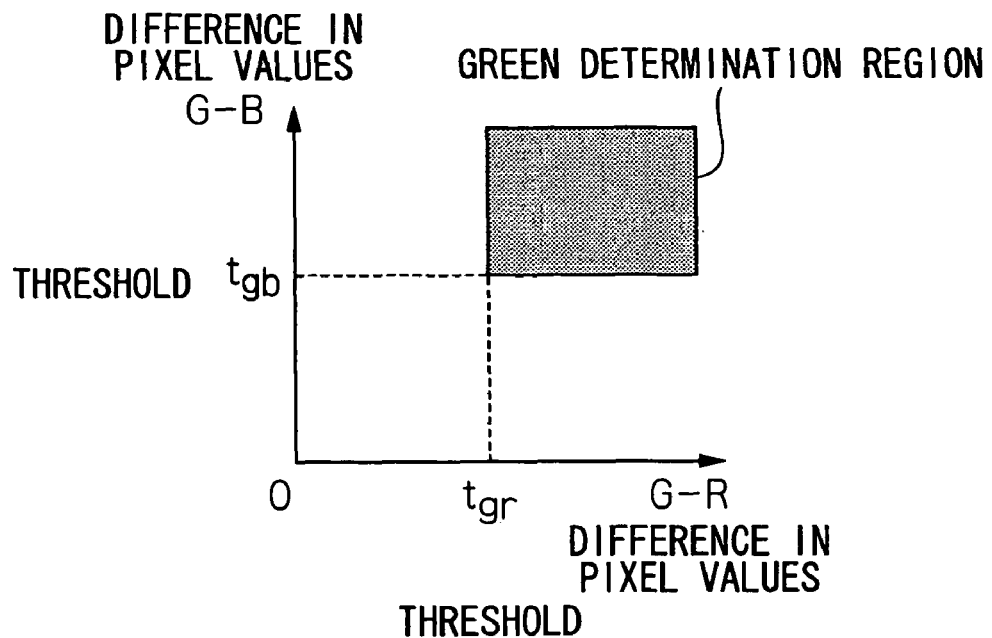
FIG. 4 is a diagram showing a green region when a threshold parameter is set.

FIG. 4 shows a green region (determination) with the threshold parameters tg.r and tg.b being set. The abscissas in the figure shows a difference in pixel values of G-R, and the ordinate shows a difference in pixel values of G-B.

When the marker M is yellow, the barycenter of the yellow region is also obtained by the expressions below.

$$C_y = \begin{bmatrix} C_{y,x} \\ C_{y,y} \end{bmatrix} \qquad \text{[Formula 2]}$$

$$= \begin{bmatrix} \dfrac{\sum_{i=1}^{W/5}\sum_{j=1}^{H/5} 5i \cdot h_y(5i, 5j)}{\sum_{i=1}^{W/5}\sum_{j=1}^{H/5} h_y(5i, 5j)} & \dfrac{\sum_{i=1}^{W/5}\sum_{j=1}^{H/5} 5j \cdot h_y(5i, 5j)}{\sum_{i=1}^{W/5}\sum_{j=1}^{H/5} h_y(5i, 5j)} \end{bmatrix}^t,$$

$$h_y(x, y) = \begin{cases} 1 & \text{if } f(x, y, g) > f(x, y, b) + t_{g,b} \text{ and} \\ & \quad f(x, y, r) > f(x, y, b) + t_{r,b} \\ 0 & \text{else} \end{cases}.$$

Tg.b, tr.b are threshold parameters to be used to detect yellow.

Figure 5:
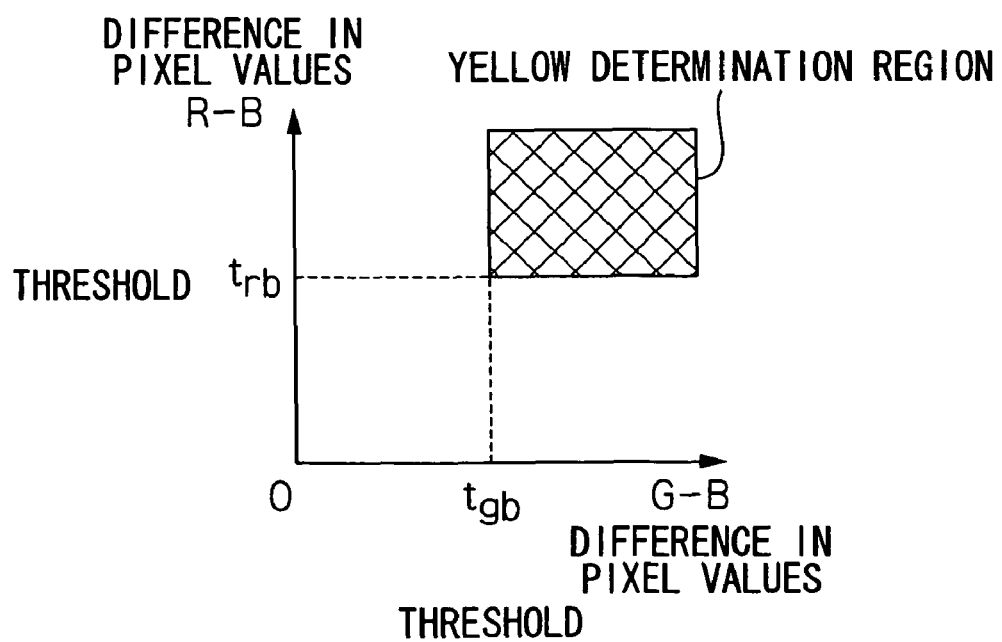
FIG. 5 is a diagram showing a yellow region when a threshold parameter is set.

FIG. 5 shows a yellow (determination) region in which the threshold parameters Tg.b, tr.b are set. The abscissas in the figure shows a difference in pixel values of G-B and the ordinate shows a difference in pixel values of R-B.

As the gravities of each color region applied with a green color and a yellow color are obtained by the calculation unit 96, the tip positions of two treatment tools 12, 12 can be detected even if the two treatment tools 12, 12 are inserted at a time.

As the pixel extracting section 94 extracts a pixel whose output value of a color component included in a color of the marker M among R, G, and B output values outputted from the CCD 58 of the observation unit 16 is bigger than the output value of a color component that is not included in a color of the marker M by a predetermined threshold or more as the group of pixels, a pixel that is actually desired to be extracted, i.e., a color of the marker M can be extracted.

Figure 6:
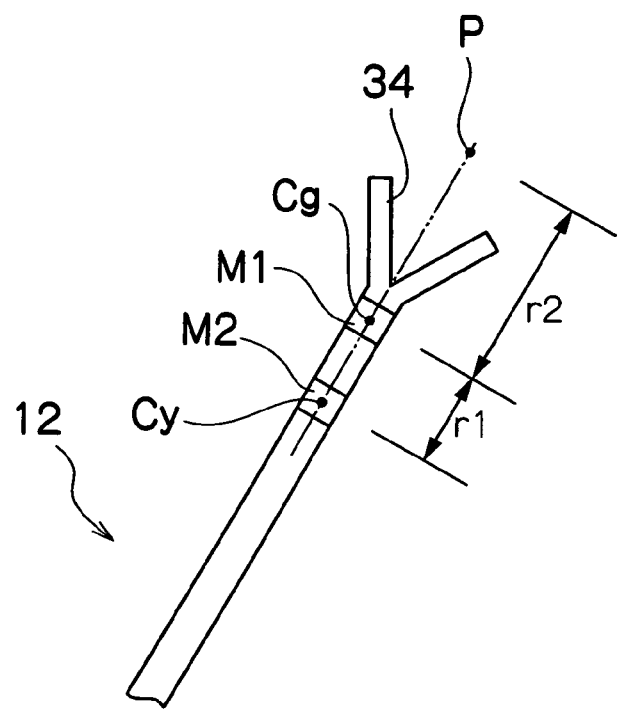
FIG. 6 is a schematic diagram showing a treatment tool applied with a green colored marker and a yellow colored marker on a single treatment tool.

On the other hand, FIG. 6 shows the treatment tool 12 added with a green marker M1 and a yellow marker M2 by predetermined interval (r1) on the tip of the treatment tool 12. If the treatment tool 12 is used, the gravities Cg, Cy against the marker M1 and the marker M2 are calculated by the abovementioned expressions. The trimming unit 86 trims an image to a predetermined region so that a position P that is away from Cg by r2 on the extension between gravities Cg and Cy is placed at the center of the image. Then, the zooming unit 88 zooms the trimmed predetermined region by a predetermined magnification on the monitor 20.

With such image processing, the predetermined region can be predicted as an actual work area by the treatment tool 12, the predicted actual work area can be zoomed and the predicted actual work area can be tracked.

Specifically, if the actual work area including the position P is F, the actual work area $$F = [F_x, F_y]^t$$

can be decided by the barycenter coordinate of a color region obtained by the calculating section 96. If the marker has a single color, $$F = Cg$$

As the markers M1 and M2 are two colors in FIG. 6, the actual work area F is predicted as linear by using the expression below.

$$F = C_y + (C_g - C_y)\frac{r_1 + r_2}{r_1} \quad \text{[Formula 3]}$$

By using the markers M1 and M2 in two colors of green and yellow, an actual work area can be predicted. If a distance r1 between the markers M1 and M2 in two colors and a distance r2 between the green marker M1 and the center position P of the actual work area F has a certain ratio of r1:r2, the actual work area F can always be calculated without regard of the position and the posture of the treatment tool 12.

Figure 7:
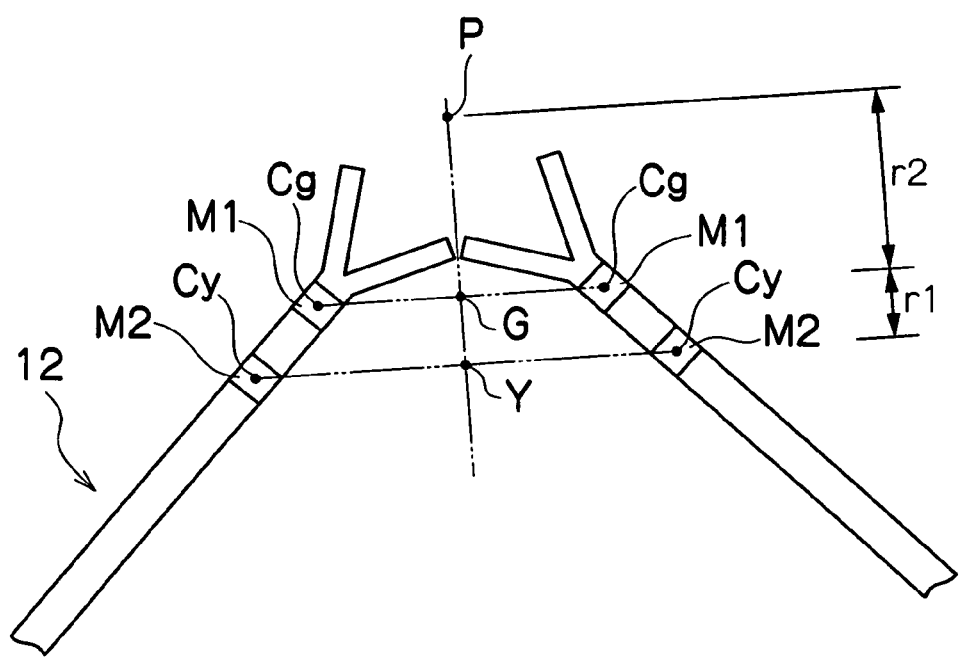
FIG. 7 is a schematic diagram showing a case where two treatment tools applied with a green colored marker and a yellow colored marker are used at a time.

The marker tracking methods can calculate the actual work area F without a problem in the similar predicting method even if two treatment tools 12, 12 are inserted at a time as shown in FIG. 7. At this moment, the system obtains the barycenter coordinate of the detected entire color region without detecting whether respective markers M1 and M2 belong to which of the treatment tools 12, 12. For example, the center point G between Cg and Cg and the center point between Cy and Cy can be calculated and the position P on the extension between G and Y can be obtained as the center of the actual work area F.

What is claimed is:

1. A body cavity observation apparatus comprising:
   a treatment tool to be inserted into a body cavity of a subject with an insertion tool as a guide,
   an observation section attached to an opening of a body wall of the subject, a monitor for displaying the body cavity captured by the observation section, and
   a marker position-detecting device for detecting a position of a marker part applied to the treatment tool or insertion tool from an image showing the body cavity captured by the observation section; wherein
   the marker position-detecting device comprises:
   a pixel extracting device for extracting a group of pixels in the same color as color of the marker part from the image, and
   a calculation device for calculating a position of the barycenter of the group of pixels as a position of the marker part; wherein
   the pixel extracting device extracts a pixel whose output value of a color component included in a color of the marker part among R, G, and B output values outputted from an image pickup device of the observation section is bigger than an output value of a color component that is not included in a color of the marker part by a predetermined threshold of the group of pixels.

2. The body cavity observation apparatus according to claim 1, further comprising:
   a trimming device for trimming an image to a predetermined region so that the position of the marker part calculated by the calculating device is placed at the center of the image, and
   a zooming device for zooming the trimmed predetermined region on the monitor by a predetermined magnification.

3. The body cavity observation apparatus according to claim 1, wherein
   the marker part is applied at least to two parts on the treatment tool or insertion tool,
   the body cavity observation apparatus includes:
   a trimming device for trimming an image to a predetermined region so that a position on a predetermined extension between two positions on the marker part calculated by the calculation device is placed at the center of the image, and
   a zooming device for zooming the trimmed predetermined region on the monitor by a predetermined magnification.

* * * * *